(12) United States Patent
Tikka (10) Patent No.: US 11,607,233 B2
(45) Date of Patent: Mar. 21, 2023

(54) ACETABULAR GUIDE

(71) Applicant: Zimmer, Inc., Warsaw, IN (US)

(72) Inventor: Vinay Tikka, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 36 days.

(21) Appl. No.: 17/114,179

(22) Filed: Dec. 7, 2020

(65) Prior Publication Data

US 2021/0169505 A1 Jun. 10, 2021

Related U.S. Application Data (60) Provisional application No. 62/946,145, filed on Dec. 10, 2019.

(51) Int. Cl.
*A61B 17/17* (2006.01)
*A61F 2/34* (2006.01)
(Continued)

(52) U.S. Cl.
CPC ............ *A61B 17/1746* (2013.01); *A61F 2/34* (2013.01); *A61B 2034/102* (2016.02);
(Continued)

(58) Field of Classification Search
CPC .. A61F 2/46; A61F 2/4657; A61F 2/32; A61F 2/34; A61F 2002/4658; A61F 2002/4659; A61F 2002/4668; A61F 2002/4687; A61F 2002/3401; A61B 17/1746; A61B 17/1742; A61B 2017/0275; A61B 34/10; A61B 2034/108;
(Continued)

(56) References Cited

U.S. PATENT DOCUMENTS

| 3,633,214 A | * | 1/1972 | Newcomb | ................ | A42B 3/14 |
| | | | | | 2/418 |
| 8,070,752 B2 | | 12/2011 | Metzger et al. | | |

(Continued)

OTHER PUBLICATIONS

Park, Yang Soo, et al., "The best method for evaluating anteversion of the acetabular component after total hip arthroplasty on plain radiographs", Journal of Orthopaedic Surgery and Research (2018) 13:66, 8 pgs https://doi.org/10.1186/s13018-018-0767-4.

(Continued)

*Primary Examiner* — Marcela I. Shirsat
(74) *Attorney, Agent, or Firm* — Schwegman Lundberg & Woessner, P.A.

(57) ABSTRACT

An orthopedic guide that can comprise a base, a first attachment and a second attachment is disclosed. The base can have a plurality of connection features spaced from one another along a longitudinal extent. The base can be configured to seat on a rim of a bone. The first attachment can be selectively coupled to the base at a first end portion thereof and can be selectively coupled to the base at a second end portion thereof. The first attachment can be arch shaped when coupled to the base. The first attachment can define a first plurality of apertures. The second attachment can be selectively coupled to the base at a first end portion thereof and can be selectively coupled to the base at a second end portion thereof. The second attachment can be arch shaped when coupled to the base. The first attachment can define a second plurality of apertures.

8 Claims, 6 Drawing Sheets

(51) Int. Cl.
*A61F 2/46* (2006.01)
*G01B 5/12* (2006.01)
*A61F 2/32* (2006.01)
*A61B 34/10* (2016.01)
*G01B 5/02* (2006.01)
*G01B 5/08* (2006.01)

(52) U.S. Cl.
CPC .......... *A61B 2034/108* (2016.02); *A61F 2/32* (2013.01); *A61F 2/4657* (2013.01); *A61F 2002/4658* (2013.01); *A61F 2002/4659* (2013.01); *A61F 2002/4668* (2013.01); *A61F 2002/4687* (2013.01); *G01B 5/025* (2013.01); *G01B 5/08* (2013.01); *G01B 5/12* (2013.01)

(58) Field of Classification Search
CPC .... A61B 2034/102; G01B 5/025; G01B 5/08; G01B 5/12; G01B 5/213
USPC ......... 606/91; 33/514.2, 512, 766, 755, 758, 33/759
See application file for complete search history.

(56) References Cited

U.S. PATENT DOCUMENTS

| | | |
|---|---|---|
| 8,092,465 B2 | 1/2012 | Metzger et al. |
| 8,282,646 B2 | 10/2012 | Schoenfeld et al. |
| 8,298,237 B2 | 10/2012 | Schoenfeld et al. |
| 8,407,067 B2 | 3/2013 | Uthgenannt et al. |
| 8,473,305 B2 | 6/2013 | Belcher et al. |
| 8,568,487 B2 | 10/2013 | Witt et al. |
| 9,345,548 B2 | 5/2016 | Schoenefeld et al. |
| 9,907,659 B2 | 3/2018 | Belcher et al. |
| 2008/0257363 A1 | 10/2008 | Schoenefeld et al. |

OTHER PUBLICATIONS

Wang, R.Y., et al., "Measurement of acetabular inclination and anteversion via CT generated 3D pelvic model", BMC Musculoskeletal Disorders (2017) 18:373, 7 pgs DOI 10.1186/12891-017-1714-y.

* cited by examiner

ACETABULAR GUIDE

CLAIM OF PRIORITY

This application claims the benefit of U.S. Provisional Patent Application Ser. No. 62/946,145, filed on Dec. 10, 2019, the benefit of priority of which is claimed hereby, and which is incorporated by reference herein in its entirety.

FIELD

The present subject matter relates to surgical apparatuses, systems and methods, and more particularly, to surgical apparatuses and related systems and methods that direct surgical instrumentation to a particular location of a surgical site.

BACKGROUND

A total femoral hip arthroplasty (THA) is a surgical procedure to repair a diseased or a damaged hip joint. A surgeon may use instruments and guides to prepare the damaged joint for receiving an orthopedic prosthesis. For example, during the THA procedure, the surgeon may ream the acetabulum of a patient to prepare a reamed area for receiving an acetabular cup prosthesis. Such reaming or implantation of the acetabular cup prosthesis may be guided by surgical guides to have a particular orientation and/or shape. The proximal head and other proximal portions of the femur can be removed. For example, the surgeon can rasp the proximal femur to provide a rasped area for receiving a femoral prosthesis that includes a stem and head portion. The prosthetic devices discussed above are then implanted recreating the hip joint on the remaining surgically prepared bone of the femur and the pelvis.

In THA, different parameters are used to place the acetabular cup and femoral prosthesis. Inclination and anteversion are important parameters that determined the quality of the THA outcome.

OVERVIEW

This disclosure pertains generally to apparatuses, systems and methods for preparing bones, such as an acetabulum in the THA, to receive the orthopedic prosthesis. Although described in relation to the THA, the apparatuses, systems and methods are applicable to other bones and joints of a patient such as the knee joint and the shoulder joint, for example.

The apparatuses, systems and methods help overcome challenges that can arise during orthopedic surgery. One such challenge can be properly locating a guide (and as a result, locating the prosthesis) taking into account a patient's anatomy (e.g., bone size, shape, inclination, anteversion, etc.). This anatomy varies from patient to patient. Appropriate inclination and anteversion for the guide can be selected in reference to natural boney anatomic landmarks. The orthopedic surgery can include orienting and placing the guide intra-operatively on top of the bone to mate, seat, be positioned relative to and/or align with corresponding boney landmarks. Thus, the boney landmarks function as passive fiducial identifiers or fiducial markers for positioning (selecting inclination and anteversion) of the guide.

Inappropriate inclination and anteversion selection may cause complications such as dependent dislocation, and in turn, cause femoroacetabular impingement syndrome (FAI). It can be time consuming and sometimes complicated for the surgeon to make appropriate anatomical measurements, adjust instruments such as the positioning of guides according to such measurements and locate the guide properly and perform other tasks related to the THA.

The present inventor has recognized, among other things, positioning guides (sometimes referred to as acetabular guides, alignment guides, drilling guides, orthopedic guides or simply as guides herein) that facilitate a desired pathway (e.g., for drilling, pin, wire and/or reaming) and resulting positioning for the acetabular cup that take into account a patient's individual anatomy. Such positioning guides can be configured to reduce surgical time and complexity as they are intuitive to use and have reduced complexity as compared with traditional guides.

According to one aspect of this application, the present inventor has recognized, among other things, orthopedic guides can benefit from being adjustable to different patient anatomies. Thus, the disclosed guides can be patient generic but can be adjustable and flexible to fit on any size of a rim of the acetabulum, for example. According to some examples, the disclosed guides can be configured to be reusable and/or easily constructible (e.g., using additive manufacturing techniques like three-dimensional printing). The present guides can be configured to help anatomic positioning and orientation (placing the acetabular cup) by adjusting parameters like inclination, anteversion to get an optimal range of motion.

According to further aspects of this application, the disclosed apparatuses, systems and methods can be utilized in tandem with imaging techniques and virtual planning tools. The imaging techniques can be using known modalities (e.g., CT, MRI, X-Ray, etc.). The imaging and virtual planning tools can facilitate the virtual identification of anatomical landmarks and/or virtual indentation of anatomical criteria such as bone size and shape, inclination, anteversion, etc. Thus, for example, the systems and methods disclosed herein can facilitate the selection of appropriate settings for selecting the inclination and/or anteversion of the guide. Thus, the present inventor has invented, apparatuses, systems and methods that include an adjustable guide and systems and methods for adjusting settings on the guide based on anatomy of the patient. In some cases, the techniques discussed can be used in combination with output from a visualization system to modify the size and/or settings of the positioning guide to be more specific to an individual patient's anatomy.

To further illustrate the apparatuses, systems and methods disclosed herein, the following non-limiting examples are provided:

Example 1 is orthopedic guide that can comprise a base, a first attachment and a second attachment. The base can have a plurality of connection features spaced from one another along a longitudinal extent. The base can be configured to seat on a rim of a bone. The first attachment can be selectively coupled to the base at a first end portion thereof and can be selectively coupled to the base at a second end portion thereof. The first attachment can be arch shaped when coupled to the base. The first attachment can define a first plurality of apertures. The second attachment can be selectively coupled to the base at a first end portion thereof and can be selectively coupled to the base at a second end portion thereof. The second attachment can be arch shaped when coupled to the base. The first attachment can define a second plurality of apertures.

Example 2 is the orthopedic guide of Example 1, wherein the first attachment and second attachment can be selectively movable relative to one another along the base to align one of the first plurality of apertures of the first attachment with one of the second plurality of apertures of the second attachment.

Example 3 is the orthopedic guide of any one or combination of Examples 1-2, wherein the base can have a first longitudinal end and a second longitudinal end opposing the first longitudinal end, wherein the base can have an arcuate shape with the first longitudinal end overlapping the second longitudinal end, and wherein the base can have a one or more second connection features configured to selectively couple with at least one of the plurality of the connection features to maintain the base in the arcuate shape.

Example 4 is the orthopedic guide of Example 3, wherein the plurality of the connection features can comprise female apertures located on at least a first side of the base and the one or more second connection features can comprise male projections located on a second side opposing the first side of the base, and wherein the male projections can be configured to mate with the female apertures.

Example 5 is the orthopedic guide of any one or combination of Examples 1-4, wherein the first attachment can be selectively coupled to a first one of the plurality of connection features at the first end portion thereof and can be selectively coupled to a second one of the plurality of connection features at the second end portion thereof, and wherein the second attachment can be coupled to a third one of the plurality of connection features at the first end portion thereof and can be selectively coupled to a fourth one of the plurality of connection features at the second end portion thereof.

Example 6 is the orthopedic guide of Example 5, wherein the base can include indicia corresponding to the plurality of connection features, wherein a first plurality of the indicia can be indicative of an inclination of the first attachment, and wherein a second plurality of the indicia can be indicative of an anteversion of the second attachment.

Example 7 is an orthopedic system that can optionally comprise a base, a first attachment and a second attachment. The base can have a plurality of connection features spaced from one another along a longitudinal extent, wherein the base can be configured to be flexible to be bent in an arcuate shape to couple a first end portion with a longitudinally opposing second end portion. The first attachment can be configured to selectively couple to a first one of the plurality of connection features at a first end portion thereof and can be configured to selectively couple to a second one of the plurality of connection features at a second end portion thereof, wherein the first attachment can define a first plurality of apertures. The second attachment can be configured to selectively couple to a third one of the plurality of connection features at a first end portion thereof and can be configured to selectively couple to a fourth one of the plurality of connection features at a second end portion thereof, wherein the first attachment can define a second plurality of apertures.

Example 8 is the orthopedic system of Example 7, wherein the first and second attachment can be arch shaped when coupled to the base, and wherein the first attachment and second attachment can be configured to be selectively movable relative to one another along the base to align one of the first plurality of apertures of the first attachment with one of the second plurality of apertures of the second attachment.

Example 9 is the orthopedic system of any one or combination of Examples 7-8, wherein when the first end portion of the base can be coupled to the second end portion of the base, a first longitudinal end of the base can overlap a second longitudinal end of the base.

Example 10 is the orthopedic system of any one or combination of Examples 7-9, wherein the base can have a one or more second connection features configured to couple with at least one of the plurality of the connection features to couple the first end portion to the second end portion.

Example 11 is the orthopedic system of Example 10, wherein the plurality of the connection features can be located on at least a first side of the base and the one or more second connection features can be located on a second side opposing the first side of the base.

Example 12 is the orthopedic system of any one or combination of Examples 7-11, wherein the base can include indicia corresponding to the plurality of connection features, wherein a first plurality of the indicia can be indicative of an inclination of the first attachment, and wherein a second plurality of the indicia can be indicative of an anteversion of the second attachment.

Example 13 is the orthopedic system of any one or combination of Examples 7-12, further optionally comprising: a computer including at least one processor and a memory device, the memory device including instructions that, when executed by the at least one processor, can cause the computer to: access image data of a target location including the bone of a patient, the image data including at least one of a bone size, a bone orientation and a bone shape; display based upon the collected image data one or more patient-specific characteristics of bone; determine an anteversion and an inclination for an acetabular implant based at least in part upon the one or more patient-specific characteristics of the bone; and convert the one or more patient-specific characteristics of the anatomy of the patient to a first setting to position the first attachment relative to the base and a second setting to position the second attachment relative to the base.

Example 14 is the orthopedic system of Example 13, further optionally comprising instructions that cause the computer to convert the one or more patient-specific characteristics of the anatomy of the patient to a third setting to determine a size of the base.

Example 15 is the system of Example 13, wherein the first setting and the second setting can each correspond to one of the plurality of connection features and comprise a first and a second of a plurality of standard settings for the first attachment and the second attachment, respectively, and the first setting and the second setting can be selected as a best match to the one or more patient-specific characteristics of the bone.

Example 16 is a method optionally comprising any one or combination of: determining a size for a base of a positioning guide; bending the base of the positioning guide to seat on a rim of a bone; determining an anteversion and an inclination from one or more patient-specific characteristics of the bone; positioning a first attachment relative to the base and the bone to achieve the anteversion; after positioning the first attachment, coupling the first attachment to the base; positioning a second attachment relative to the base and the bone to achieve the inclination; after positioning the second attachment, coupling the second attachment to the base; and guiding an instrument to the bone at the inclination and the anteversion using an aperture of the first attachment that is aligned with an aperture of the second attachment.

Example 17 is the method of Example 16, further optionally comprising coupling a first longitudinal end portion of the to a second opposing longitudinal end of the base to achieve the size of the base.

Example 18 is the method of any one or combination of Examples 16-17, further optionally comprising: imaging the bone to collect image data regarding at least one of a bone size, a bone orientation and a bone shape of the patient; determining based upon the collected image data one or more patient-specific characteristics of the bone; and converting the one or more patient-specific characteristics of the anatomy of the patient to a first setting to position the first attachment relative to the base and a second setting to position the second attachment relative to the base.

Example 19 is the method of Example 18, further optionally comprising converting the one or more patient-specific characteristics of the anatomy of the patient to a third setting to determine the size of the base.

Example 20 is any one or combination of features or elements of the Examples 1-19.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to guides, methods and systems for preparing a bone during an orthopedic procedure. For example, the acetabular guides of the present application can reference various anatomical portions of the hip and can include attachments with guiding holes, bores, slots, or other guiding formations (collectively termed simply "apertures" herein) that can accurately position a drill, a guide wire, a pin, etc., for later acetabular preparation and implantation procedures and for alignment purposes, including implant version control and implant inclination control.

Figure 1:
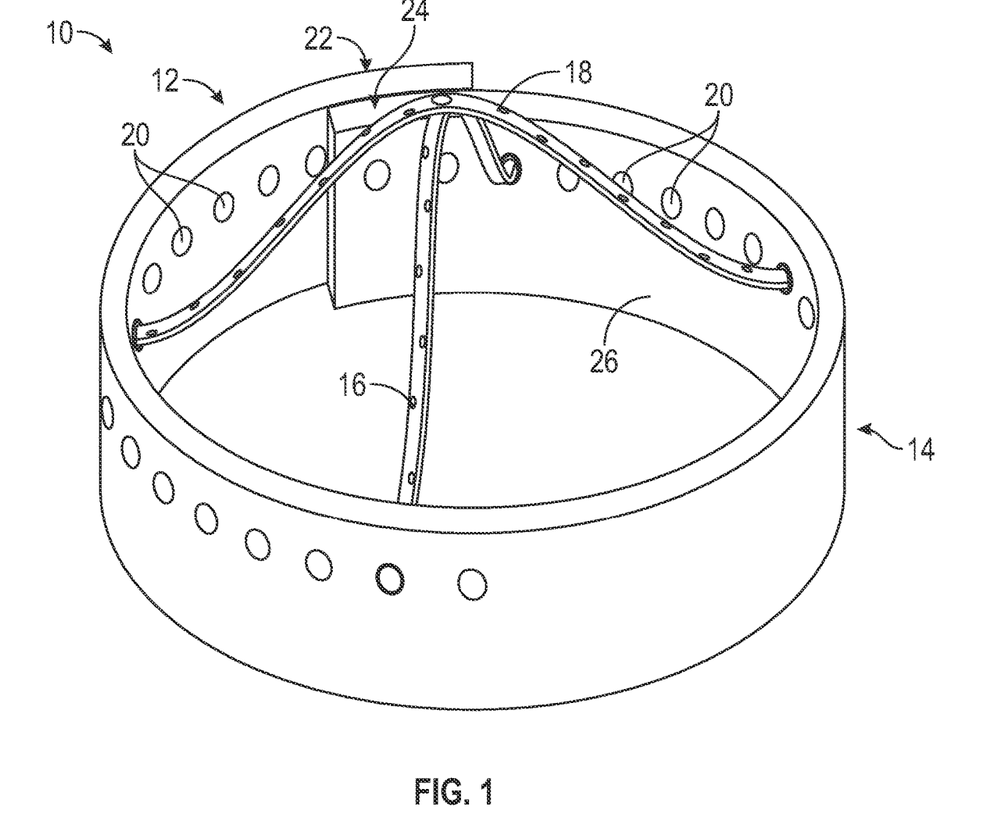
FIG. 1 is a perspective view of a guide having a base and first and second attachments, in accordance with an example of the present disclosure.

FIG. 1 shows a perspective view of a guide 10 according to an example of the present application. The guide 10 can be configured as an acetabular guide 12 according to the example. The guide 10 can include a base 14, a first attachment 16 and a second attachment 18. The base 14 can include a first plurality of connection features 20.

Figure 5:
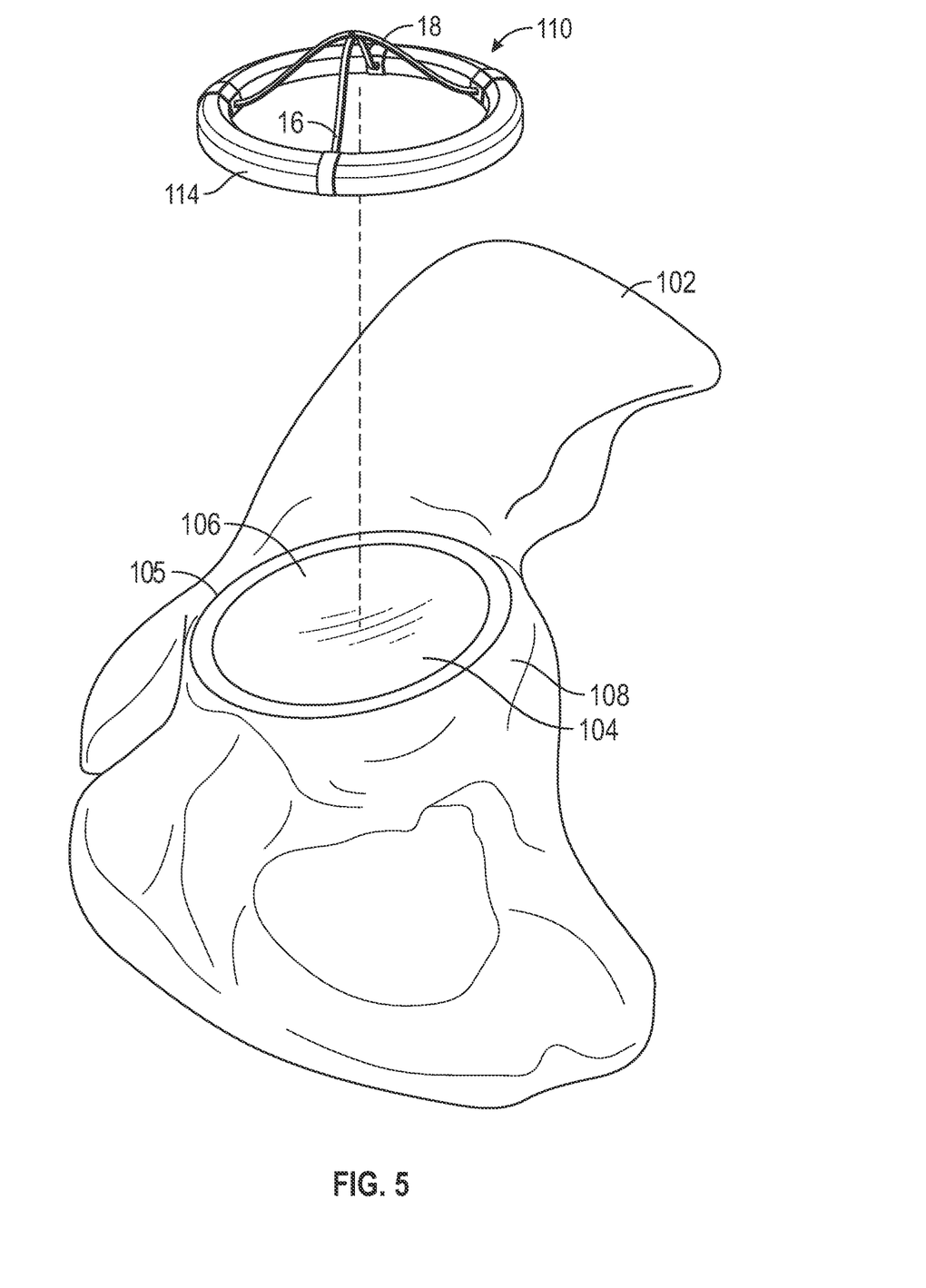
FIG. 5 is a perspective view of another example of the guide positioned over an acetabulum, in accordance with an example of the present disclosure.
Figure 6:
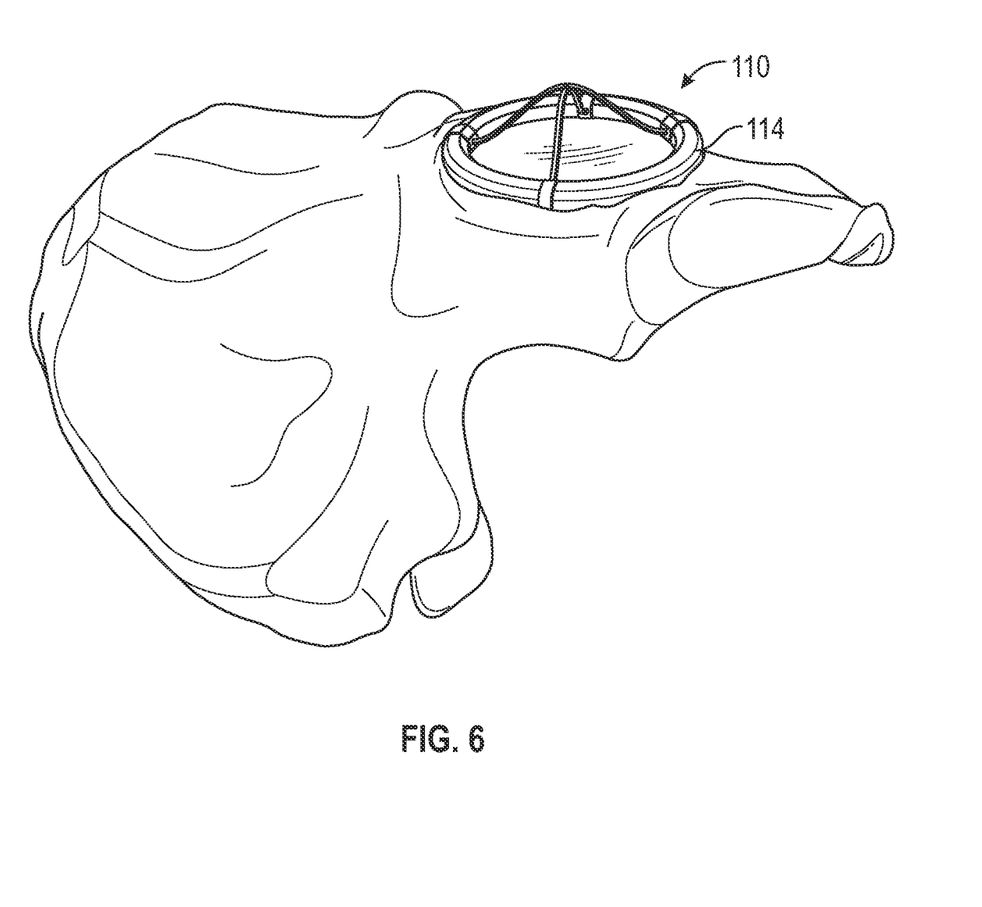
FIG. 6 is a perspective view of the guide coupled to a rim of the acetabulum, in accordance with an example of the present disclosure.

According to the example of FIG. 1, the base 14 can comprise a belt or member and can be formed by a surgeon to a shape and size configured to seat on a bone such as a rim of an acetabulum of a pelvis (illustrated in FIGS. 5 and 6). Such forming (e.g., bending and/or sizing) can be performed by the surgeon such as intraoperatively during the THA and can be done with reference to one or more patient-specific characteristics of the anatomy of the patient such as bone (e.g., acetabular rim) size and/or bone shape, for example.

The base 14 can be formed of biologically stable material (s) such as a polymer (e.g., nylon), metal, metal alloy and/or composite, for example. As shown in FIG. 1, the base 14 can have a first end portion 22 configured to couple with a second end portion 24. This coupling of the first end portion 22 with the second end portion 24 can be facilitated via flexing/bending of the base 14 to an arcuate shape (shown as the coupled position illustrated in FIG. 1). The location of the coupling between the first end portion 22 and the second end portion 24 can be determined by an amount of overlap between the end portions 22 and 24 and can determine the size of the base 14. Put another way, the surgeon can select to have more or less overlap between the first end portion 22 and the second end portion 24 as desired to determine the size of the base 14.

The first plurality of connection features 20 can be arranged along an inner side surface 26 of the base 14. The connection features 20 can comprise mechanisms known in the art (e.g., apertures of various types such as holes, slots, bores, receptacles, etc., projections of various types such as hooks, fasteners, fingers, jaws, etc., snares/loops, buttons, snaps, adhesive, or the like) for mechanical coupling. The first plurality of connection features 20 can be used according to some examples to couple the first end portion 22 with the second end portion 24. According to further examples, the first plurality of connection features 20 can couple the first attachment 16 to the base 14 and can couple the second attachment 18 with the base 14.

The first attachment 16 can be configured as an arch, for example. The first attachment 16 can be selectively coupled to the base 14 at a first end portion thereof and selectively coupled to the base 14 at a second end portion thereof.

Similarly, the second attachment 18 can be configured as an arch, for example. The second attachment 18 can be selectively coupled to the base 14 at a first end portion thereof and selectively coupled to the base 14 at a second end portion thereof. The operation and constructions of the first attachment 16 and the second attachment 18 are further discussed in regard to FIGS. 3 and 4.

FIGS. 2A-2D show plan views of the base 14 in isolation according to one example. FIGS. 2A-2D are broken away views illustrating the first end portion 22 and the second end portion 24 and not a full elongate extent of the base 14. Thus, the base 14 can include more of the first plurality of connection features 20 than are illustrated. Different shapes and types of elements for the first plurality of connection features 20 are contemplated. FIG. 2E shows a cross-sectional view of the base 14. In FIGS. 2A-2E, the base 14 is shown in an uncoupled or unconnected state. Thus, the first end portion 22 is not coupled to the second end portion 24 in the uncoupled state as shown in FIGS. 2A-2E. Rather, the base 14 can be arranged as an uncoupled belt or track without arc or turn having an elongate extent along a longitudinal axis LA or elongate axis.

In addition to the first end portion 22 and the second end portion 24, the base 14 can have a first end 28 on a first end of the elongate extent and a second end 30 on a second end of the elongate extent. The first end 28 can oppose the second end 30. The first end 28 can be part of the first end portion 22. The first end portion 22 can also include one or more of the first plurality of connection features 20. The second end 30 can be part of the second end portion 24. The second end portion 24 can include one or more of a plurality of connection features 21. The base 14 can include a bottom or distal surface 32 shown in FIGS. 2A and 2E. As shown in FIG. 2E, the distal surface 32 can be shaped as a saddle 34 or other feature to facilitate connection to bone. Put another way, the distal surface 32 via the saddle 34 can be configured to seat on the rim of the acetabulum as further illustrated herein.

Figure 2A:
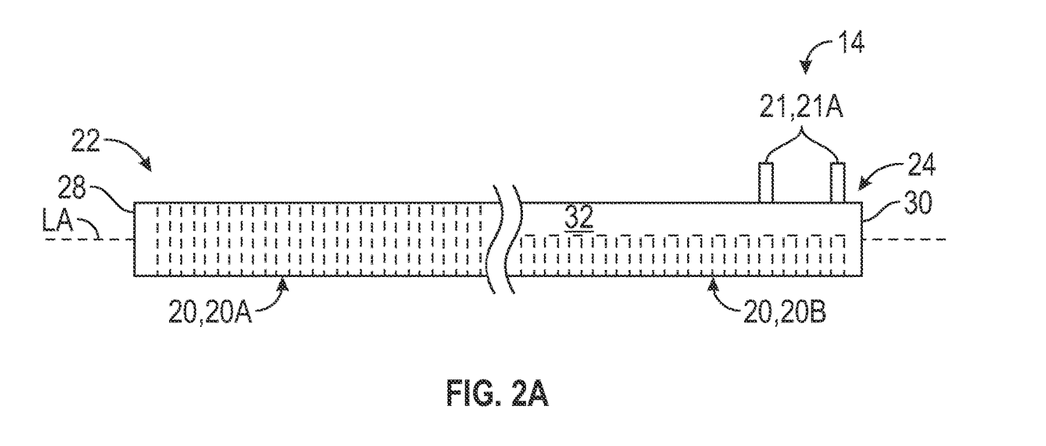
FIG. 2A is a first plan view of a distal side of the base of the guide of FIG. 1 in an uncoupled state, in accordance with an example of the present disclosure.

FIG. 2A shows the first plurality of connection features 20 can be spaced from one another along the longitudinal extent (longitudinal axis LA). Similarly, if two or more of second plurality of connection features 21 are utilized, these can be spaced from one another along the longitudinal extent. One or more of the first plurality of connection features 20 can comprise apertures such as apertures 20A and apertures 20B (shown in phantom in FIG. 2A). One or more of the second plurality of connection features 21 can comprise one or more projections 21A. The projections 21A can be configured to couple with, mate or otherwise connection with the apertures 20A. This can occur, for example, when the base 14 is flexed/bent to the coupled position of FIG. 1. This coupling of the projections 21A with the apertures 20A can maintain the base 14 in the coupled position. Such coupling between the projection(s) 21A and the apertures 20A can be a snap-fit or interference type fit, for example. Thus, the base 14 can have one or more second connection features 21 configured to selectively couple with at least one of the plurality of the connection features 20. This coupling can maintain the base 14 in the arcuate (coupled position) of FIG. 1.

Figure 2B:
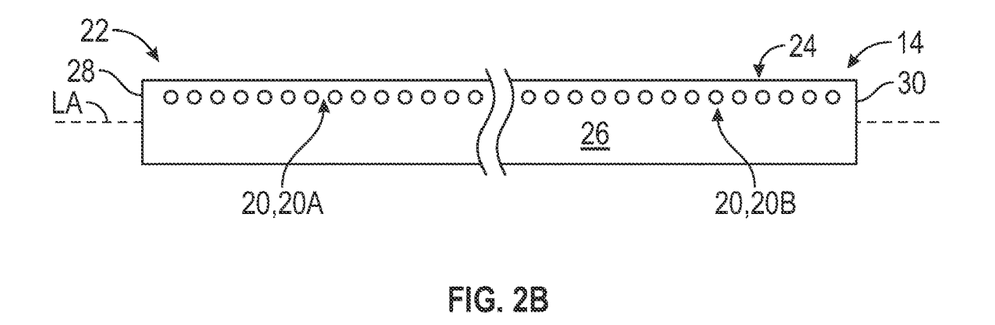
FIG. 2B is a second plan view of an interior side of the base of the guide of FIG. 1 in the uncoupled state, in accordance with an example of the present disclosure.

FIG. 2B shows the inner side surface 26 of the base 14 previously illustrated in FIG. 1 in further detail. The inner side surface 26 can have the first plurality of connection features 20 such as the apertures 20A and 20B. Although the apertures 20A are illustrated as extending entirely through the base 14 as shown in FIGS. 2A and 2B, it is contemplated that the apertures 20A may not extend entirely through the base 14 and can be constructed in the manner of apertures 20B. According to further examples, the apertures 20A and/or 20B can be another mechanical feature other than an aperture such as projections, buttons etc. as previously discussed. It should be noted that fewer or more (or various types) of the first plurality of connection features 20 can be utilized according to other examples.

Figure 2C:
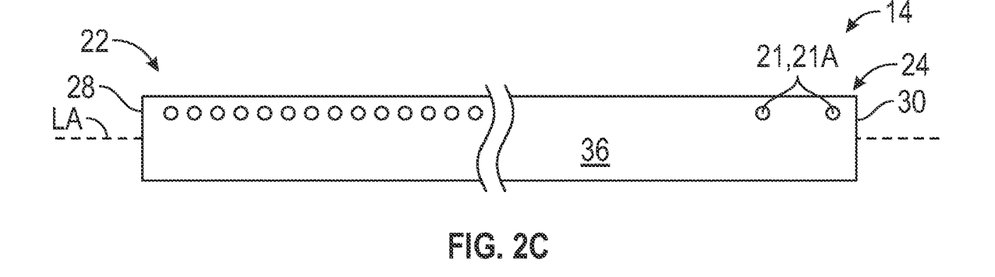
FIG. 2C is a third plan view of an exterior side of the base of the guide of FIG. 1 in the uncoupled state, in accordance with an example of the present disclosure.

FIG. 2C shows an outer side surface 36 of the base 14. The outer side surface 36 can oppose the inner side surface 26 across a thickness of the base 14. The outer side surface 36 can include at least one or more of the second plurality of connection features 21. For example, the projections 21A can extend outward from the outer side surface 36. The one or more of the second plurality of connection features 21 can be another mechanical feature other than projections such as apertures, buttons etc. The one or more of the second plurality of connection features 21 can be any feature configured to mate with the first plurality of connection features 20, for example. It should be noted that fewer or more (or various types) of the one or more of the second plurality of connection features 21 can be utilized according to other examples. In the example of FIG. 2C, the apertures 20A can extend through the base 14 and can communicate with the outer side surface 36.

The base 14 can be fabricated as the belt or track in the uncoupled state of FIGS. 2A-2D using additive manufacturing techniques like three-dimensional printing, for example. As discussed above, the base 14 can be formed of flexible material (e.g., nylon or other polymer, shape memory polymer, metal or metal alloy, etc.) and can be flexed/bent and sized by the surgeon during the THA.

Figure 2D:
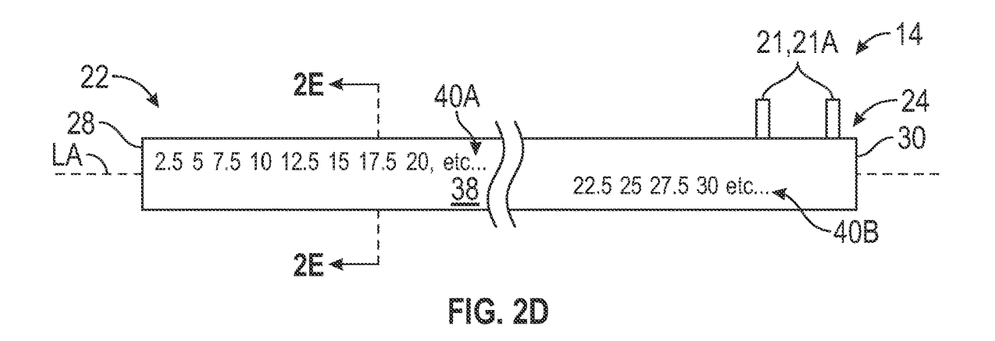
FIG. 2D is a fourth plan view of a distal side of the base of the guide of FIG. 1 in the uncoupled state, in accordance with an example of the present disclosure.
Figure 2E:
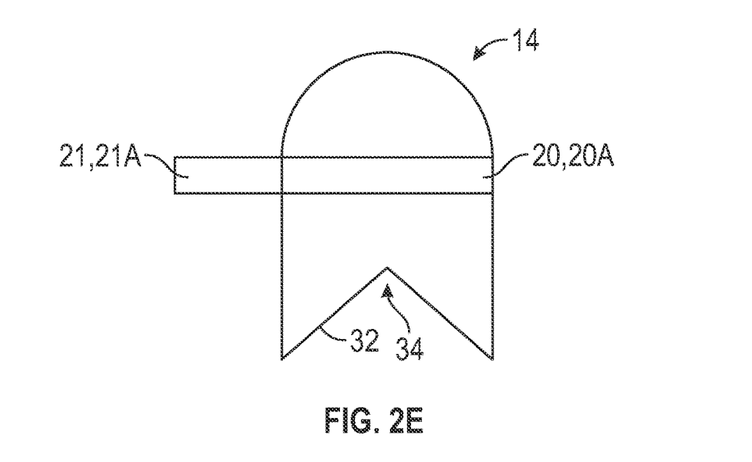
FIG. 2E is a cross-sectional view of the base of the guide along lines 2E-2E of FIG. 2D, in accordance with an example of the present disclosure.

FIG. 2D shows a top or proximal surface 38 of the base 14. The proximal surface 38 can be flat, chamfered or otherwise shaped. As shown in the example of FIG. 2D, the top surface 38 (or another surface of the base 14) can include indicia 40A and/or 40B. The indicia 40A can be indicative of different degrees of anteversion. The degree of anteversion achieved by the guide 10 can be between 0 degrees and 40 degrees, inclusive, for example. More particularly, the indicia 40A can comprise a plurality of markings (e.g. angle markings, letters, numbers, etc.). Each of the indicia 40A can correspond to a particular one of the first plurality of connection features 20, for example. Thus, for example, the indicia "5" indicates 5 degree angle of anteversion and corresponds to a particular one of the first plurality of connection features 20 (a particular one of the apertures 20A). The indicia 40B can be indicative of different degrees of inclination. The degree of inclination achieved by the guide 10 can be between 22 degrees and 55 degrees, inclusive, for example. More particularly, the indicia 40B can comprise a plurality of markings (e.g. angle markings, letters, numbers, etc.). Each of the indicia 40B can correspond to a particular one of the first plurality of connection features 20, for example. Thus, for example, the indicia "22" indicates a 22 degree angle of inclination and corresponds to a particular one of the first plurality of connection features 20 (a particular one of the apertures 20A or apertures 20B). Further discussion regarding surgeon selection of inclination and anteversion is discussed in regard to FIGS. 3 and 7, for example. Appropriate inclination and anteversion for the guide 10 can be selected in reference to natural boney anatomic landmarks. The orthopedic surgery can include orienting and placing the guide 10 intra-operatively on top of the bone (e.g., on the rim of the acetabulum as shown in FIG. 6) to mate with the bone. The first attachment 16 (FIGS. 1 and 3) and the second attachment 18 (FIGS. 1 and 3) can be selectively positioned as desired such as to align or be otherwise positioned relative with patient anatomy such as corresponding boney landmarks. These boney landmarks can comprise any one or combination of an anterior superior iliac spine, pubic tubercle(s), and/or sacral crest(s), for example. Thus, the boney landmarks function as passive fiducial identifiers or fiducial markers for positioning (selecting inclination and anteversion) of the guide. The first attachment 16 (FIGS. 1 and 3) and the second attachment 18 (FIGS. 1 and 3) can be selectively positioned as desired relative to these landmarks or relative to other anatomy or virtually generated features such as sagittal, coronal and/or transverse planes, best fit ellipses and other features. A methodology for selecting anteversion and inclination is discussed for example in the article entitled "THE BEST METHOD FOR EVALUATING ANTEVERSION OF THE ACETABULAR COMPONENT AFTER TOTAL HIP ARTHROPLASTY ON PLAIN RADIOGRAPHS" in the Journal of Orthopaedic Surgery and Research, published Apr. 2, 2018 and the article entitled "MEASUREMENT OF ACETABULAR INCLINATION AND ANTEVERSION VIA CT GENERATED 3D PELVIC MODEL", published Aug. 29, 2017 and found online at https://www.ncbi.nlm.nih.gov/pmc/articles/PMC5576350/, the entire contents of both of which are incorporated herein by reference in their entirety.

Figure 3:
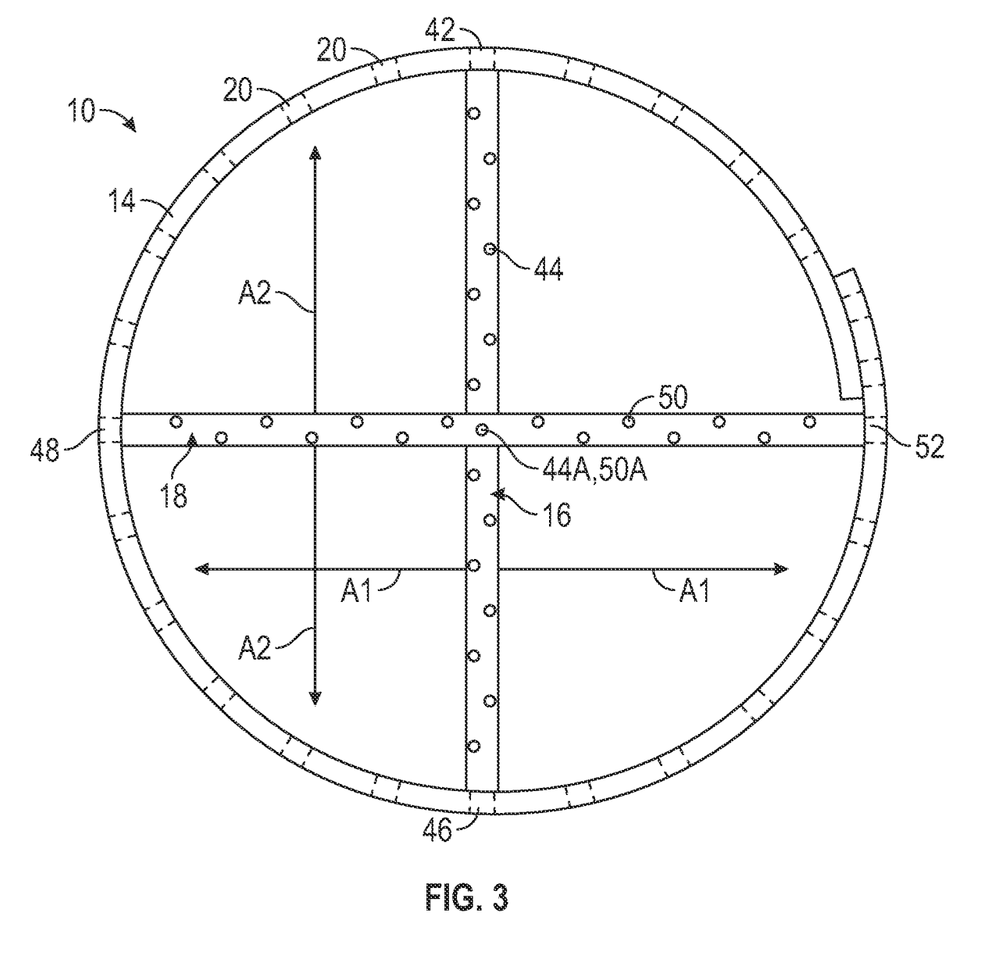
FIG. 3 is a schematic view of the guide of FIG. 1 illustrating adjustment of the first and second attachments to achieve a desired inclination and anteversion for the guide, in accordance with an example of the present disclosure.
Figure 4:
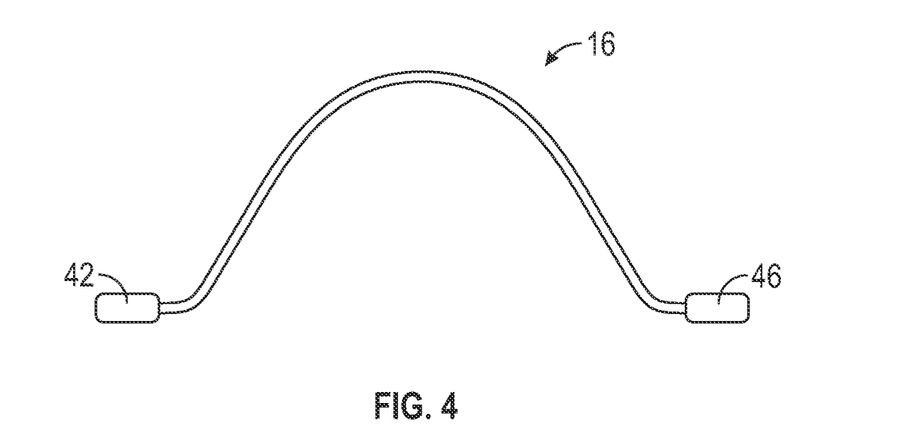
FIG. 4 is a side view of one of the first attachment member or the second attachment member, in accordance with an example of the present disclosure.

FIG. 3 shows the guide 10 from an elevated position with the first attachment 16 and the second attachment 18 selectively coupled to the base 14. FIG. 4 shows a side plan view of the first attachment 16. The first attachment 16 can include a first end portion 42, a first plurality of apertures 44 (FIG. 3) and a second end portion 46. As shown in FIG. 3, the second attachment 18 can include a first end portion 48, a second plurality of apertures 50 and a second end portion 52.

In FIG. 3, the first attachment 16 can be configured to be selectively movable so as to be positionally adjustable relative to the base 14 and the second attachment 18. Similarly, the second attachment 18 can be configured to be selectively movable relative so as to be positionally adjustable relative to the base 14 and the first attachment 16. The movement of first attachment 16 is shown by arrows A1 and can be used to change the inclination of the first attachment 16 as further discussed subsequently. The movement of the second attachment 18 is shown by arrows A2 and can be used to change the anteversion of the second attachment 18 as further discussed subsequently.

As discussed previously, the first attachment 16 and the second attachment 18 can be arch shaped when coupled to the base 14. More particularly, the first attachment 16 and the second attachment 18 can be formed of a flexible material(s) such as those of the base 11 so as to be configured to bend to the arch shape shown in FIGS. 1, 3 and 4 from an unbent fabricated shape, for example. It should be noted that the first attachment 16 can be positionally adjustable (movable as shown by arrows A1) in a manner that is facilitated by the flexing of the first attachment 16. Similarly, the second attachment 18 can be positionally adjustable (movable as shown by arrows A2) in a manner that is facilitated by the flexing of the first attachment 18. More particularly, when moved along arrow A1 the first attachment 16 can become relative more flexed or unflexed. Thus, first end portion 42 and the second end portion 46 can become relatively closer together or further apart from one another. Furthermore, the apex of the arch formed by the first attachment 16 can be relatively closer (lower) or further away (higher) relative to the base 14. Similarly, when moved along arrow A2 the second attachment 18 can become relatively more flexed or unflexed. Thus, first end portion 48 and the second end portion 52 can become relatively closer together or further apart from one another. Therefore, the apex of the arch formed by the first attachment 18 can be relatively closer (lower) or further away (higher) relative to the base 14.

The first plurality of apertures 44 can be spaced from one another along an elongate length of the first attachment 16 from adjacent the first end portion 42 to adjacent the second end portion 46. Similarly, the second plurality of apertures 50 can be spaced from one another along an elongate length of the second attachment 18 from adjacent the first end portion 48 to the adjacent the second end portion 52. The first end portions 42, 48 and the second end portions 46, 52 can be configured to couple with the first plurality of connection features 20 (some of which are shown in phantom in FIG. 3) to facilitate connection of the first attachment member 16 and the second attachment member 18 to the base 14. For example, the end portions 42, 48 and the second end portions 46, 52, can be insertable in respective ones of the first plurality of connection features 20.

The first plurality of apertures 44 can comprise guiding holes, bores, slots, or other guiding formations that are configured to position a drill, a guide wire a pin, etc. for later acetabular preparation and implantation procedures and for alignment purposes with the desired inclination. Similarly, the second plurality of apertures 50 can comprise guiding holes, bores, slots, or other guiding formations that are configured to position the drill, the guide wire, the pin, etc. for later acetabular preparation and implantation procedures and for alignment purposes with the desired anteversion. As shown in FIG. 3, the first attachment 16 and second attachment 18 can be selectively movable relative to one another along (e.g., around) the base 14 to align one aperture 44A of the first plurality of apertures 44 of the first attachment 16 with one aperture 50A of the second plurality of apertures 50 of the second attachment 18. This one aperture 44A of the first plurality of apertures 44 and the one aperture 50A of the second plurality of apertures 50 can have both the desired anteversion and the desired inclination for the drill, the guide wire, the pin, etc.

FIG. 5 shows another example of a guide 110. The guide 110 can have a same construction as the guide 10 previously discussed save for the differences noted below. In particular, the guide 110 can have a base 114 that need not be sized and shaped by the physician during the THA as with guide 10 but can rather be fabricated with a size and shape that is patient-specific or available in a number of standard sizes. Put another way, imaging and surgical planning can be performed prior to fabrication of base 114 can be performed according to some examples to make it patient-specific. Thus, fabrication of the base 114 can be done with reference to one or more patient-specific characteristics of the anatomy of the patient such as bone (e.g., acetabular rim) size and/or bone shape, for example. Thus, base 114 can have a fixed size and/or shape (e.g., having a ring shape) unlike the base 14 of the prior examples.

Another difference between the guide 110 and the guide 10 is that the first plurality of connection features 20 of the guide 110 are not utilized to couple the first attachment 16 to the base 114 and the second attachment 18 to the base 114. Rather the first attachment 16 and the second attachment 18 can couple over the base 114 such as by snapping over a proximal surface of the base 114.

FIG. 5 illustrates a pelvis 102 of a specific patient. An acetabulum 104 of the pelvis 102 is also illustrated. The acetabulum 104 can include a rim 105 and a reference surface or prepared bone surface 106 therein. The prepared bone surface 106 can be prepared using any suitable instrument, such as a reamer, in order to prepare the acetabulum 104 to receive an implant. The acetabulum 104, the rim 105, the prepared bone surface 106 thereof, and portions of the pelvis 102 surrounding the acetabulum 104 together generally can define an implantation site 108. The implantation site 108 can include various features, such as a recess in the bone and the rim 105 of the acetabulum 101, for example.

The pelvis 102 including the acetabulum 104, the rim 105 and the prepared bone surface 106 can be of any suitable size and shape based on the patient's anatomy. In some cases, a type or size of implant can dictate a size and shape of the prepared bone surface 106. The size and shape of the guide 110, such as diameter, shape of a distal bone mating surface and orientation of the attachments 16 and 18, can be of any suitable size or shape to correspond to the implantation site 108. According to one example, at least the base 114 can be patient-specific as previously discussed. Thus, the implant site 108 can receive the base 114 in only a single patient-specific orientation pursuant to the preoperative plan. Orientation of the first attachment 16 and the second attachment 18 can be determined by the surgeon with reference to the anatomy during the THA or can be determined preoperatively according to the preoperative plan and using imaging and/or virtual planning tools as discussed further in FIG. 7. The orientation and of the first attachment 16 and the second attachment 18 can guide the drill, the guide wire, the pin, etc. (and hence, the prosthesis) to the acetabulum 104 for implantation at a predetermined orientation having the desired inclination and desired anteversion as previously discussed. Various other instruments not specifically shown can be utilized to properly size, select and couple the acetabular implant to the pelvis 102 including inserters, drills, etc., which are commercially available from Zimmer Biomet, Warsaw, Ind.

FIG. 6 shows the guide 110, and in particular the base 114, mounted/seated on the rim 105 (FIG. 5) of the acetabulum 104 (FIG. 5).

Figure 7:
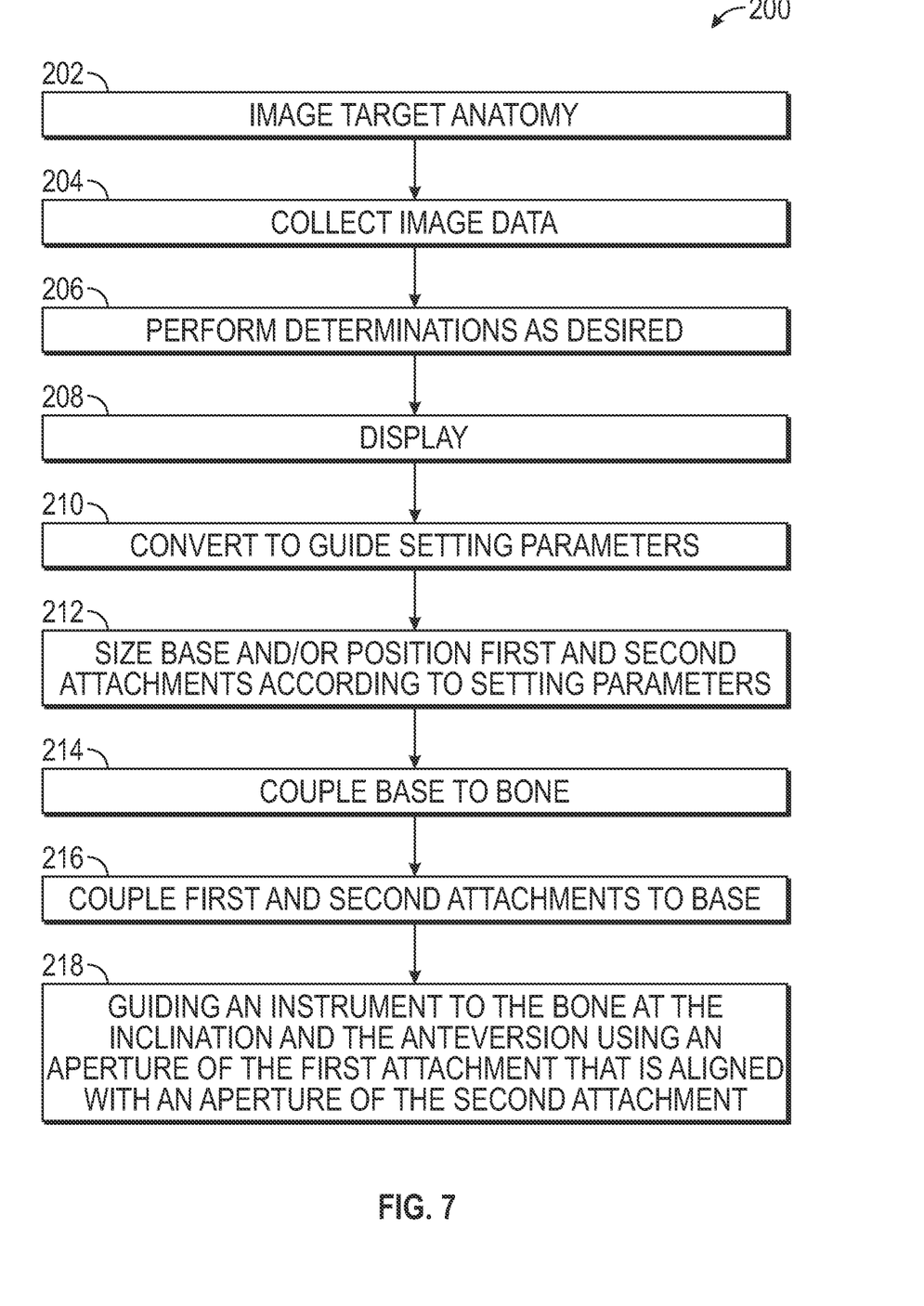
FIG. 7 is a flow chart of a method of using a guide to guide an instrument to the bone at a desired inclination and a desired anteversion, in accordance with an example of the present disclosure.

FIG. 7 shows a methodology that can be implemented by the guide 10 or the guide 110. In particular, the guide 10 or 110 can be used as part of systems and methods of generating and outputting data comprising position settings and/or size settings for purposes of tailoring the guide 10 or 110 such that the guide can be used to create a patient appropriate implant orientation having a desired orientation (e.g., the desired inclination and anteversion). It should be noted, however, that the method of FIG. 7, including the virtual surgery planning systems and methods discussed herein are optional and the guide 10 or 110 can be used without them.

The guide disclosed herein can be aided by the use of computer-assisted image methods based on two-dimensional or three-dimensional images of the patient's bones and/or adjacent anatomy generated by magnetic resonance imaging ("MRI"), computer tomography ("CT"), ultrasound, X-ray, or other medical imaging techniques. Various computer aided drafting ("CAD") programs and/or other software can be utilized for the image reconstruction of the anatomy (in three-dimensions or two-dimensions) from the medical scans of the patient, such as, for example, commercially available software.

Various pre-operative planning procedures and related patient-specific instruments are disclosed in commonly assigned and pending or now issued U.S. patent application Ser. No. 11/756,057, filed May 31, 2007; U.S. patent application Ser. No. 11/971,390, filed on Jan. 9, 2008; U.S. patent application Ser. No. 12/025,414, filed on Feb. 4, 2008; U.S. patent application Ser. No. 12/039,849 filed on Feb. 29, 2008; U.S. patent application Ser. No. 12/103,824, filed Apr. 16, 2008; U.S. patent application Ser. No. 12/371,096, filed Feb. 13, 2009; U.S. patent application Ser. No. 12/483,807, filed Jun. 12, 2009; U.S. patent application Ser. No. 12/872,663, filed Aug. 31, 2010; U.S. patent application Ser. No. 12/973,214, filed Dec. 20, 2010; and U.S. patent application Ser. No. 12/978,069, filed Dec. 23, 2010. The disclosures of the above applications are incorporated herein by reference in their entirety.

The systems and methods can draw upon preoperative surgical plans. These plans can be formulated for a specific patient. A preoperative surgical plan can encompass virtual surgery planning with the aid of a computer, as will be discussed subsequently. The systems and method can allow for interactive input from the patient's physician or other medical professional according to some examples. Imaging data from medical scans of the relevant anatomy of the patient can be obtained at a medical facility or doctor's office, using any of the medical imaging techniques discussed previously. The imaging data can include, for example, various medical scans of a relevant bone (here the pelvis 102), bones or other relevant portion of the patient's anatomy, as needed for virtual anatomy modeling and, optionally, for virtual determination of resection size, shape (e.g. angle) and relative orientation. The imaging data, thus obtained, and other associated information can be used to construct a computer (digital) image of the anatomy of the patient. The preoperative surgical plan can further include the identification and selection of particular bone portions that need to be removed or retained, virtual orientation (in regards to at least anteversion and inclination) of the guide and/or orthopedic device as disclosed herein on the pelvis, virtual implantation of the guide and/or the orthopedic implant, etc. Such selections such as a selection to determine a length/size of the guide and/or orientation of the guide can be made to best match the patient's anatomical need. For example, the disclosed guide including the attachments can be configured to have various settings to adjust the orientation (in regards to at least anteversion and inclination) of the apertures for guiding. The base of the guide can include settings corresponding to one or more of the connection features to determine orientation of the first and second attachments and also to facilitate shaping/sizing the guide as previously discussed in reference to FIGS. 1-4. Such settings can be standard settings that are not necessarily patient-specific, but can be adjusted based on data output to the physician comprising various size and/or orientation settings that most closely match the needs of the patient based upon the patient's anatomy. These size and/or orientation settings can be visually displayed to the physician as part of the surgical plan. Thus, referring back to the example of FIGS. 2D and FIG. 3, the appropriate ones of the one or more connection features 20 can be virtually determined. If the inclination based upon patient-specific anatomy such as the boney anatomic landmarks is determined to be 22 degrees, the virtual surgery planning aid would display a setting of 22 indicating the applicable attachment should be coupled to the one of the plurality of connection features with the indicia 22 as shown in FIG. 2D. A similar methodology can be utilized to set the anteversion and/or the size of the base.

The virtual model of the patient's anatomy can be viewed on a computer display or other electronic screen and can also be reproduced as a hard copy on disk or other medium and viewed by direct or indirect or backlight illumination. The model can be sized for viewing on any appropriate screen size and may be cropped, rotated, etc., as selected by the individual (e.g., the physician) viewing the screen. The three-dimensional model can illustrate diseased bone that should be removed and can identify the shape and orientation of the resection(s) to be used in removal of the diseased bone, etc. The three-dimensional model can further illustrate the guide overlaid on the bone such as in FIG. 6 and can show the relevant orientations of the first and second attachments according to one example.

As previously discussed, the orthopedic device 100 can be fabricated with various standard markings or indicia such as those of FIG. 2D indicative of corresponding ones of the plurality of connection features 20. A marking "22" (or another value) of the base 14 can correspond to a virtual output "22" (or another value) displayed to the user. Put another way, the base 14 can be set to a most appropriate inclination (as determined virtually) as indicated or suggested by the system output. A similar methodology can be utilized regarding anteversion.

According to one example, a method is disclosed that optionally utilizes imaging data from a patient and performs calculations from the imaging data including determining locations of bone geometry and structure. From the calculations, surgical decisions including the positioning of instruments such as the first and second attachments of the guide 10, 110 can be determined. The surgical decisions can be visualized electronically prior to being implemented. Based upon the visualization, the physician can alter his or her decision as desired.

FIG. 7 shows a flow chart of a method 400 according to one example of the present application. The method 200 can include aspects for virtual surgery planning and implementation using the guide 10 or guide 110, for example. However, as noted above the virtual surgical planning aspects of the method 200 are optional and may not be utilized in many cases.

At a high level, the example of FIG. 7 can optionally include: determining a size for a base of a positioning guide; bending the base of the positioning guide to seat on a rim of a bone; determining an anteversion and an inclination from one or more patient-specific characteristics of the bone; positioning a first attachment relative to the base and the bone to achieve the anteversion; after positioning the first attachment, coupling the first attachment to the base; positioning a second attachment relative to the base and the bone to achieve the inclination; after positioning the second attachment, coupling the second attachment to the base; and guiding an instrument to the bone at the inclination and the anteversion using an aperture of the first attachment that is aligned with an aperture of the second attachment.

As is further illustrated in the example of FIG. 7, imaging 202 can be performed of the patient's anatomy of interest (a target location) using any one or combination of the technology previously discussed. Such scanning can collect image data 204 of the patient's anatomy of interest. Such image data can include at least one of a bone size, a bone orientation (at least anteversion and inclination) and a bone shape of the patient, for example. The collected image data can be stored such as in a database, file or other known medium including the Cloud. Image processing of the image data can be performed as desired (e.g., to sharpen or contrast the image, to better identify anatomical surface features, etc.). The method 200 can perform calculations 206 to describe and/or characterize the geometry and/or orientation of bone in the anatomy of interest. The calculations can be performed upon the stored image data corresponding to the target location. These calculations can determine or describe, for example, patient-specific characteristics such as bone dimensions, bone axes/landmarks/positions, relative positions between bone portions, curvature and surface topography of the bone surface, and/or soft tissue attachment size and/or location, bone orientation of particular boney landmarks (discussed previously), and the like. According to further examples, the calculations can be used to determine and/or describe the geometry and other characteristics of diseased bone that may require removal. According to some examples, the calculations can be used to determine and/or describe the geometry, orientation and other characteristics of bone that may not be removed during the procedure and can determine the patient-specific characteristics of that bone, in addition to or in alternative to the diseased bone.

The method 200 can determine 206 appropriately-sized, shaped and/or oriented resections (one or more) to remove the diseased bone. Such determination can consider patient-specific characteristics regarding both the diseased bone and/or any adjacent bone that may be retained. The method can display 208 data to a physician or other personnel. For example, the display 208 can include a patient-appropriate setting(s) (e.g., what location along the base 14 to insert and couple the first attachment 16, what location along the base 14 to insert and couple the second attachment 18, what is an appropriate size for the base 14, etc.) for the guide 10 as previously illustrated as described. According to another example, the display step 208 can include displaying data about the anatomy of interest and/or data regarding the area of interest to a physician or other personnel. Such displaying can further include display of patient-specific characteristics (e.g., diseased and/or healthy bone dimensions, bone orientation, surface topography, or the like). In some examples, displaying can include virtual assembly and/or arrangement of the guide on the anatomy of interest, for example. The displaying can further include display of patient-specific characteristics (dimensions, orientation including at least inclination and anteversion, etc.) of the one or more resections, or other aspects of the pelvis, which can be based at least in part upon the one or more patient-specific characteristics of the anatomy of the patient.

Method 200 can further convert 210 various of the patient-specific characteristics (e.g., size, shape, orientation including at least inclination and anteversion, etc.) to corresponding setting parameters (e.g. relative length(s), shape, anteversion setting for the first attachment, inclination setting for the second attachment, etc.) for the guide 10 or 110. According to some examples, the corresponding setting parameters can be displayed so that the appropriate setting can be made to the guide 10 or 110.

FIG. 7 also shows implementation of the method 200 to perform guiding an instrument to the bone at the inclination and the anteversion using an aperture of the first attachment that is aligned with an aperture of the second attachment. This can be done with or without the virtual surgical planning of steps 202-210 as discussed previously. At step 212, the base can be sized and the first and second attachment can be positioned relative to one another and/or the base. At step 214, the base can be coupled to bone. At step 216, the base and the first and second attachments can be coupled together according to the positional settings. This process can be done based upon physician measurement inspection during the THA. Alternatively, the sizing, positioning and/or coupling can be done according to the setting parameters provided by the virtual surgical planning tool. The method 200 can guide 218 an instrument to the bone at the inclination and the anteversion using an aperture of the first attachment that is aligned with an aperture of the second attachment.

Additional Notes

Certain examples are described herein as including logic or a number of components, modules, or mechanisms. Modules may constitute either software modules (e.g., code embodied on a machine-readable medium or in a transmission signal) or modules. A module is tangible unit capable of performing certain operations and may be configured or arranged in a certain manner. In examples, one or more computer systems (e.g., a standalone, client or server computer system) or one or more modules of a computer system (e.g., a processor or a group of processors) may be configured by software (e.g., an application or application portion) as a module that operates to perform certain operations as described herein.

In various examples, a module may be implemented mechanically or electronically. For example, a module may comprise dedicated circuitry or logic that is permanently configured (e.g., as a special-purpose processor, such as a field programmable gate array (FPGA) or an application-specific integrated circuit (ASIC)) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in dedicated and permanently configured circuitry, or in temporarily configured circuitry (e.g., configured by software) may be driven by cost and time considerations.

Accordingly, the term "module" can be understood to encompass a tangible entity, such as hardware, that can be that an entity that is physically constructed, permanently configured (e.g., hardwired) or temporarily configured (e.g., programmed) to operate in a certain manner and/or to perform certain operations described herein. Considering examples in which modules are temporarily configured (e.g., programmed), each of the modules need not be configured or instantiated at any one instance in time. For example, where the modules comprise a general-purpose processor configured using software, the general-purpose processor may be configured as respective different modules at different times. Software may accordingly configure a processor, for example, to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In examples in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some examples, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example examples, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Examples may be implemented in digital electronic circuitry, or in computer hardware, firmware, software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of examples may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various examples.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An orthopedic system comprising:
   a base having a plurality of connection features spaced from one another along a longitudinal extent, wherein the base is configured to be flexible to be bent in an arcuate shape to couple a first end portion with a longitudinally opposing second end portion;
   a first attachment configured to selectively couple to a first one of the plurality of connection features at a first end portion thereof and configured to selectively couple to a second one of the plurality of connection features at a second end portion thereof, wherein the first attachment defines a first plurality of apertures; and
   a second attachment configured to selectively couple to a third one of the plurality of connection features at a first end portion thereof and configured to selectively couple to a fourth one of the plurality of connection features at a second end portion thereof, wherein the second attachment defines a second plurality of apertures;
   wherein the base includes indicia corresponding to the plurality of connection features, wherein a first plurality of the indicia are indicative of an inclination of the first attachment, and wherein a second plurality of the indicia are indicative of an anteversion of the second attachment.

2. The orthopedic system of claim 1, wherein the first and second attachment are arch shaped when coupled to the base, and wherein the first attachment and second attachment are configured to be selectively moveable relative to one another along the base to align one of the first plurality of apertures of the first attachment with one of the second plurality of apertures of the second attachment.

3. The orthopedic system of claim 1, wherein when the first end portion of the base is coupled to the second end portion of the base, a first longitudinal end of the base overlaps a second longitudinal end of the base.

4. The orthopedic system of claim 1, wherein the base has a one or more second connection features configured to couple with at least one of the plurality of the connection features to couple the first end portion to the second end portion.

5. The orthopedic system of claim 4, wherein the plurality of the connection features are located on at least a first side of the base and the one or more second connection features are located on a second side opposing the first side of the base.

6. An orthopedic system comprising:
   a base having a plurality of connection features spaced from one another along a longitudinal extent, wherein the base is configured to be flexible to be bent in an arcuate shape to couple a first end portion with a longitudinally opposing second end portion;
   a first attachment configured to selectively couple to a first one of the plurality of connection features at a first end portion thereof and configured to selectively couple to a second one of the plurality of connection features at a second end portion thereof, wherein the first attachment defines a first plurality of apertures;

a second attachment configured to selectively couple to a third one of the plurality of connection features at a first end portion thereof and configured to selectively couple to a fourth one of the plurality of connection features at a second end portion thereof, wherein the second attachment defines a second plurality of apertures;

a computer including at least one processor and a memory device, the memory device including instructions that, when executed by the at least one processor, cause the computer to:

access image data of a target location including a bone of a patient, the image data including at least one of a size of the bone, an orientation of the bone and a shape of the bone;

display based upon the collected image data one or more patient-specific characteristics of the bone;

determine an anteversion and an inclination for an acetabular implant based at least in part upon the one or more patient-specific characteristics of the bone; and convert the one or more patient-specific characteristics of the anatomy of the patient to a first setting to position the first attachment relative to the base and a second setting to position the second attachment relative to the base.

7. The orthopedic system of claim 6, further comprising instructions that cause the computer to convert the one or more patient-specific characteristics of the anatomy of the patient to a third setting to determine a size of the base.

8. The orthopedic system of claim 6, wherein the first setting and the second setting each correspond to one of the plurality of connection features and comprise a first and a second of a plurality of standard settings for the first attachment and the second attachment, respectively, and the first setting and the second setting are selected as a best match to the one or more patient-specific characteristics of the bone.

* * * * *